US007831395B2

(12) United States Patent
Zhou et al.

(10) Patent No.: US 7,831,395 B2
(45) Date of Patent: *Nov. 9, 2010

(54) QUANTIFICATION OF ADSORBED MOLECULAR CONTAMINANT USING THIN FILM MEASUREMENT

(75) Inventors: Lin Zhou, LeGrangeville, NY (US); Eric P. Solecky, Hyde Park, NY (US)

(73) Assignee: International Business Machines Corporation, Armonk, NY (US)

( * ) Notice: Subject to any disclaimer, the term of this patent is extended or adjusted under 35 U.S.C. 154(b) by 247 days.

This patent is subject to a terminal disclaimer.

(21) Appl. No.: 12/046,542

(22) Filed: Mar. 12, 2008

(65) Prior Publication Data

US 2008/0154519 A1 Jun. 26, 2008

Related U.S. Application Data

(63) Continuation of application No. 11/423,844, filed on Jun. 13, 2006, now Pat. No. 7,369,947.

(51) Int. Cl.
*G06F 17/00* (2006.01)

(52) U.S. Cl. ......................... 702/27; 702/170; 438/514; 73/432.1; 427/255.7; 428/447; 324/755

(58) Field of Classification Search ................... 702/27, 702/170; 438/782, 514, 709, 725, 790, 114, 438/692, 17, 14; 73/432.1, 73; 427/255.7; 257/48; 428/447, 472.2, 137; 324/755, 754, 324/765, 235

See application file for complete search history.

(56) References Cited

U.S. PATENT DOCUMENTS

| | | | | |
|---|---|---|---|---|
| 6,508,990 | B1 * | 1/2003 | Yoshida et al. | 422/186.05 |
| 6,809,032 | B1 * | 10/2004 | Mauersberger et al. | 438/692 |
| 6,835,642 | B2 * | 12/2004 | Yang et al. | 438/601 |
| 7,092,077 | B2 * | 8/2006 | Kishkovich et al. | 356/36 |
| 7,270,886 | B2 * | 9/2007 | Lee et al. | 428/447 |
| 7,319,942 | B2 * | 1/2008 | Hatfield et al. | 703/2 |
| 2004/0224537 | A1 * | 11/2004 | Lee et al. | 438/782 |
| 2004/0259029 | A1 * | 12/2004 | Nagahara et al. | 430/270.1 |
| 2005/0114101 | A1 * | 5/2005 | Hatfield et al. | 703/2 |
| 2005/0183490 | A1 * | 8/2005 | Grayfer et al. | 73/23.2 |
| 2006/0093730 | A1 * | 5/2006 | Phan et al. | 427/8 |
| 2007/0215801 | A1 * | 9/2007 | Walsh et al. | 250/252.1 |
| 2007/0281498 | A1 * | 12/2007 | Lee et al. | 438/782 |

* cited by examiner

*Primary Examiner*—Carol S Tsai
(74) *Attorney, Agent, or Firm*—Scully, Scott, Murphy & Presser, P.C.; Joseph Petrokaitis, Esq.

(57) ABSTRACT

A test method for measuring adsorbed molecular contamination uses a test structure that includes a substrate comprising a plurality of separated test sites having a plurality separate thicknesses having a base design thickness and a designed thickness interrelationship. The test structure is exposed to a molecular contaminant environment to provide an adsorbed molecular contaminant layer upon each of the plurality of separated test sites. The plurality of separated test sites with the adsorbed molecular contaminant layer thereon is measured. An appropriate algorithm that considers the designed thickness interrelationship is used to determine at least one of: (1) the base design thickness; and (2) a thickness of the adsorbed molecular contaminant layer.

7 Claims, 2 Drawing Sheets

QUANTIFICATION OF ADSORBED MOLECULAR CONTAMINANT USING THIN FILM MEASUREMENT

CROSS REFERENCE OF RELATED APPLICATIONS

This application is a continuation of U.S. patent application Ser. No. 11/423,844, filed Jun. 13, 2006.

BACKGROUND

1. Field of the Invention

The invention relates generally to microelectronic fabrication. More particularly, the invention relates to adsorbed molecular contaminant film measurement within microelectronic fabrication.

2. Description

The process of fabricating microelectronic structures, and in particular semiconductor structures, typically requires the use of a variety of materials and related process environments, the materials include wet chemical materials as well as dry plasma materials. Process environments include ambient environments as well as vacuum environments.

As a result of using multiple process environments, microelectronic structures are typically exposed to, or transferred within, process environments that may prove to be contaminant environments with respect to subsequent environments within which they are processed. The process environments provide for adsorption of molecular contaminants which are often particularly detrimental. They are particularly undesirable when they are strongly adsorbed or otherwise unable to be desorbed prior to a subsequent process that otherwise requires an atomically clean or chemically reproducible surface for subsequent processing.

Quantification of adsorbed molecular contaminants thus provides an important challenge within microelectronic structure and semiconductor structure fabrication.

Adsorbed molecular contamination may be quantified using any of several quantification methods. Included are optical ellipsometry methods, thermal desorption methods and secondary ion mass spectroscopy methods.

While each of the foregoing quantification methods provides value within the context of adsorbed molecular contaminations determination, needs continue to exist for generally simplified apparatus and methods that allow for direct quantification of adsorbed molecular contamination. It is to that end that the invention is directed.

SUMMARY OF THE INVENTION

The invention provides a test method for quantifying adsorbed molecular contamination. The test method may also be used for determining a base design thickness for a series of test sites within a test structure. The method uses the test structure that comprises a substrate comprising a plurality of separated test sites. The plurality of separated test sites has a base design thickness, and a plurality of separate thicknesses related thereto by means of a designed thickness interrelationship. The test structure is placed in a molecular contaminant environment to allow a layer of molecular contaminant to adsorb upon the plurality of test sites A thickness of each of the plurality of test sites including the layer of adsorbed molecular contaminant is then measured. At least one of: (1) a thickness of the adsorbed molecular contaminant layer; and (2) the base designed thickness, is determined using an algorithm that considers the designed thickness interrelationship between the plurality of test sites. The adsorbed molecular contaminant may include moisture, or an alternative adsorbed organic molecular contaminant such as but not limited to an alcohol or a ketone.

The method is particularly applicable to quantification of adsorbed molecular contamination upon a gate dielectric material layer that may be used within a semiconductor structure.

A method in accordance with the invention includes exposing a test structure comprising a substrate comprising a plurality of separated test sites having a plurality of separate thicknesses having a base design thickness and a designed thickness interrelationship to a molecular contaminant environment to provide an adsorbed molecular contaminant layer upon each of the plurality of separated test sites. The method also includes measuring heights of the plurality of separated test sites with the adsorbed molecular contaminant layer thereon. The method also includes determining at least one of: (1) a thickness of the adsorbed molecular contaminant layer; and (2) the base design thickness within the designed thickness interrelationship, while using an algorithm that considers the designed thickness interrelationship.

BRIEF DESCRIPTION OF THE DRAWINGS

The objects, features and advantages of the invention are understood within the context of the Description of the Preferred Embodiment, as set forth below. The Description of the Preferred Embodiment is understood within the context of the accompanying drawings, which form a material part of this disclosure, wherein.

DESCRIPTION OF THE PREFERRED EMBODIMENT

The invention, which includes a method for quantifying adsorbed molecular contamination while using a particular absorbed molecular contaminant test structure, is disclosed in further detail within the context of the description provided below. The description provided below is understood within the context of the drawings described above. The drawings are intended for illustrative purposes, and as such are not necessarily drawn to scale.

FIG. 1 to FIG. 7 show a series of schematic cross-sectional diagrams illustrating the results of progressive stages of fabrication and use of an adsorbed molecular contaminant test structure in accordance with the preferred embodiment of the invention.

Figure 1:
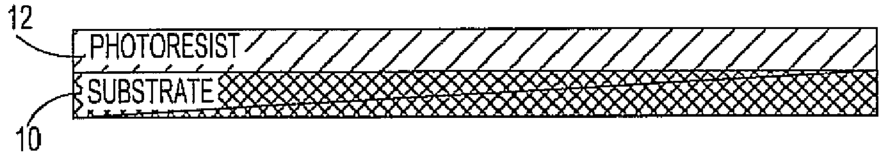
FIG. 1 to FIG. 7 show a series of schematic cross-sectional diagrams illustrating the results of progressive stages in fabricating and using an adsorbed molecular contaminant test structure in accordance with a preferred embodiment of the invention.

FIG. 1 shows a substrate 10. A first photoresist layer 12 is located upon the substrate 10.

The substrate 10 may comprise any of several materials. Non-limiting examples include conductor materials, semiconductor materials and dielectric materials. For convenience of use within semiconductor fabrication, the substrate 10 typically comprises a semiconductor substrate. Preferably, the substrate 10 has a comparatively low affinity for an adsorbed molecular contaminant material desired to be quantified in accordance with the invention.

The first photoresist layer 12 may comprise any of several photoresist materials. Non-limiting examples include positive photoresist materials, negative photoresist materials and hybrid photoresist materials. Typically, the first photoresist layer 12 is formed using conventional spin-coating and thermal curing methods that provide the first photoresist layer 12 with a thickness from about 1000 to about 20000 angstroms.

Figure 2:
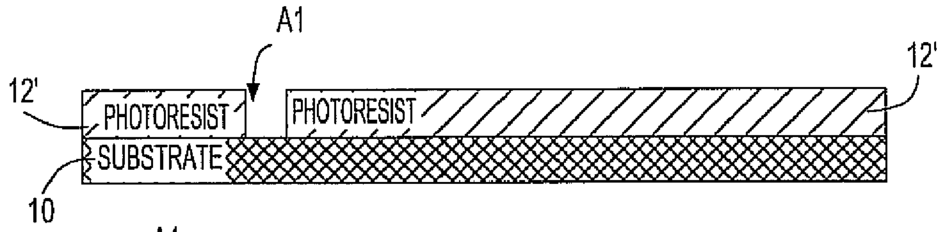

FIG. 2 shows the results of photoexposing and developing the first photoresist layer 12 to yield first photoresist layer 12' that exposes the substrate 10 at the bottom of a first aperture A1. The first aperture A1 typically has a linewidth from about 10 to about 100 microns. The photoexposing and developing of the first photoresist layer 12 to provide the first aperture A1 is undertaken using generally conventional methods and materials.

Figure 3:
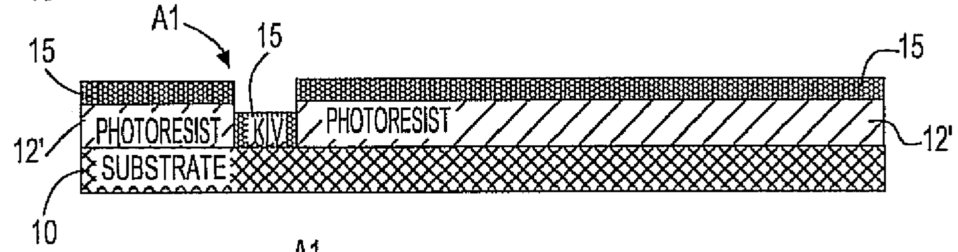

FIG. 3 shows the results of depositing a first test material layer 15 (i.e., a first test site) upon the semiconductor structure of FIG. 2 and in particular partially filling the first aperture A1. Similarly with the substrate 10, the first test material layer 15 may comprise any one of a conductor material, a semiconductor material and a dielectric material. Typically, the test material is selected as a material that may be of particular importance with respect to adsorbed molecular contamination determination within a manufacturing process. Within the context of a semiconductor manufacturing process, a dielectric material, such as a dielectric material having a composition that may be used within a gate dielectric layer, is often of particular importance.

Within the embodiment, the first test material layer 15 is deposited with a thickness K1V, where V is intended as a base design thickness (which may be experimentally determined and verified as an actual value) and K1 is intended to designate a multiplier for the base design thickness V. For example and without limitation, a base design thickness V may be in a range from about 10 to about 50 angstroms, and a first multiplier K1 for the base design thickness may be an integral multiplier or a non-integral multiplier. Typically, K1 equals unity.

Figure 4:
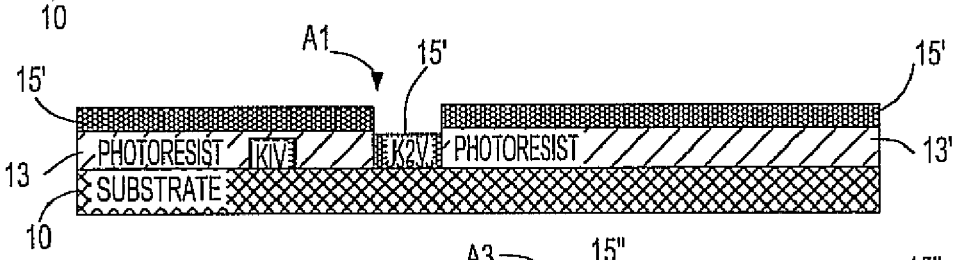

FIG. 4 shows an additional sequence of processing that corresponds with the sequence of processing of FIG. 2 to FIG. 3, but with a second photoresist layer 13 that has a second aperture A2 therein laterally separated from the first aperture A1. FIG. 4 also illustrates a second test material layer 15' that has a second thickness K2V. Similarly with the first thickness K1V, the second thickness K2V also comprises a base design thickness V and a second multiplier K2. Thus, the first test material layer 15 and the second test material layer 15' are interrelated in thickness by a first multiplier K1 and a second multiplier K2 with respect to a base design thickness V.

Figure 5:
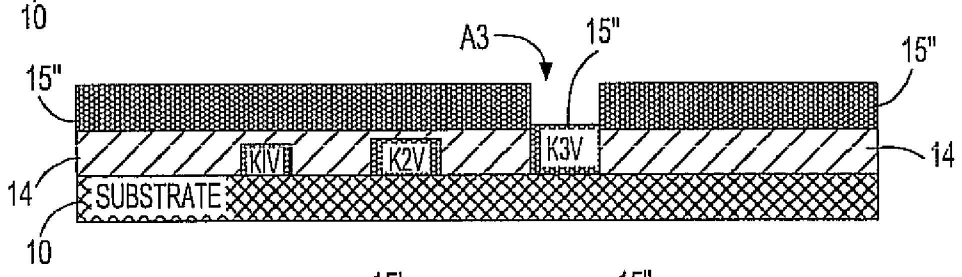

FIG. 5 shows an additional sequence of processing that corresponds with the sequence of processing of FIG. 2 to FIG. 3, but with a third photoresist layer 14 and a third test material layer 15". The third photoresist layer 14 is otherwise analogous or equivalent to the second photoresist layer 13 or the first photoresist layer 12', but the third photoresist layer 14 defines a third aperture A3 separated from the second aperture A2 and the first aperture A1. In accordance with disclosure above, the third test material layer 15" has a third thickness K3V, where, again, V is a base design thickness and K3 is a third multiplier. Thus, each of the first test material layer 15, the second test material layer 15' and the third test material layer 15" is interrelated to a base design thickness V by way of the corresponding first multiplier K1, second multiplier K2 and third multiplier K3 (i.e., a designed thickness interrelationship). Typically, although not exclusively, the first multiplier K1, the second multiplier K2 and the third multiplier K3 are integrally related.

Figure 6:
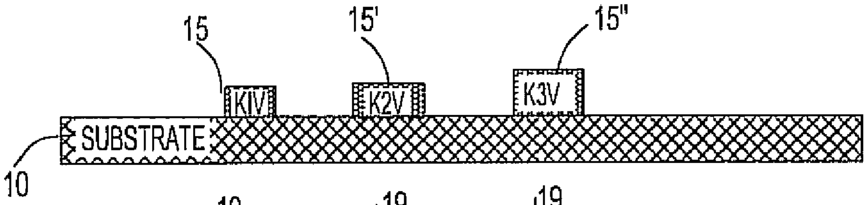

FIG. 6 shows the results of stripping excess portions of the third test material layer 15" from the third photoresist layer 14 and then stripping the third photoresist layer 14 from the substrate 10.

FIG. 6 thus shows a test structure that comprises a substrate 10 having a series of first, second and third test material layers 15, 15' and 15" located thereupon. Within the invention, the substrate 10 may comprise any of several materials, including but not limited to: conductor materials, semiconductor materials and dielectric materials. Similarly, the first, second and third test material layers 15, 15' and 15" may also comprise any of several test materials (i.e., conductor, semiconductor or dielectric), hut they are all formed of the same material preferably deposited identically.

Figure 7:
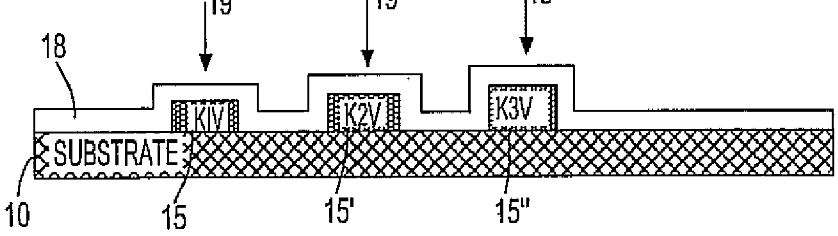

FIG. 7 shows a schematic cross-sectional diagram illustrating the results of exposing the test structure of FIG. 6 within a test environment that comprises a concentration of a molecular contaminant that absorbs upon the test material layers 15, 5' and 15". The adsorbed molecular contaminant forms adsorbed molecular contaminant layer 18, having a nominally identical thickness S upon each of the test material layers 15, 15' and 15".

In accordance with the invention a total film thickness measurement is made for each of the composite layers comprising a first, second or third test material layer 15, 15' or 15" and the adsorbed molecular contaminant layer 18 (i.e., 15/18, 15'/18 and 15"/18). The thickness of the individual composite layers are T1=K1V+S, T2=K2V+S and T3=K3V+S (i.e., in general Tm,n=Km,nV+S, where m,n equal 1, 2, 3 . . . etc.). The measurements may be made using an ellipsometry method, an optical scattering method, an ion beam method or an alternative quantification method having an appropriate resolution. The thickness measurement uses a measurement beam 19 that is nominally perpendicular to the plane of the substrate 10. In light of the foregoing equations, actual values for V (i.e., base design thickness) and S (i.e., adsorbed contaminant layer thickness) may be calculated using any two test structures Km and Kn having any two thicknesses Tm and Tn as follows.

$$V=(Tm-Tn)/(Km-Kn)$$

$$S=-(KnTm-KmTn)/(Km-Kn)$$

The foregoing process and measurement are subject to measurement variation within the context of only two data points. Thus, a regression analysis may be used for purposes of reducing measurement variations.

Figure 8:
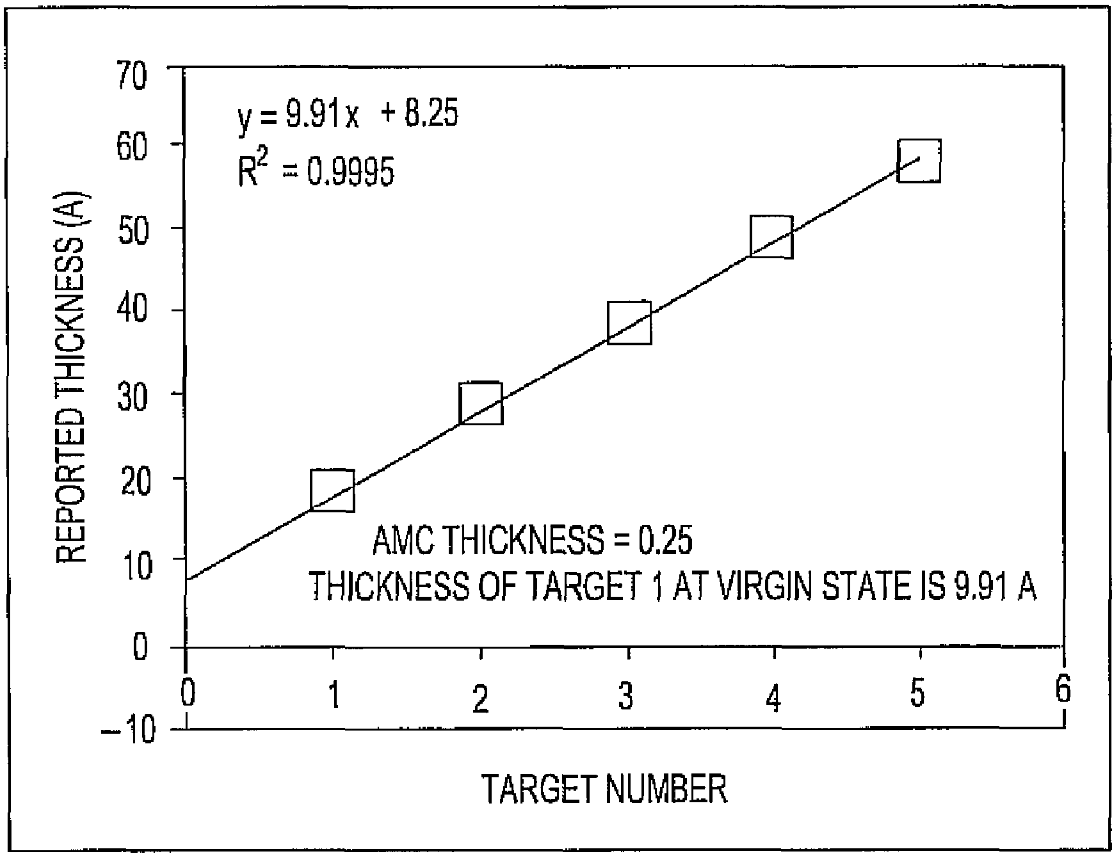
FIG. 8 show a graph of Reported Thickness versus Target Number illustrating the results of using an adsorbed molecular contaminant test structure in accordance with the invention.

The result of such a regression analysis is shown in the graph of FIG. 8. In general the graphical analysis uses the linear regression equation: Tn=V*Kn+S.

For the graph of FIG. 8, an intercept S is equal to 8.25 angstroms as the actual measured value of the adsorbed molecular contaminant layer. A slope is equal to 9.91 angstroms which equates to the base design thickness V.

The preferred embodiment of the invention is illustrative of the invention rather than limiting of the invention. Revisions and modifications may be made to methods, materials, structures and dimensions in accordance with the preferred embodiment of the invention, while still providing an embodiment in accordance with the invention, further in accordance with the accompanying claims.

What is claimed is:

1. A test system comprising:

a test structure comprising a substrate comprising a plurality of separated test sites having a plurality of separate thicknesses having a base design thickness and a designed thickness interrelationship, the test structure being susceptible to absorption of a molecular contaminant within a molecular contaminant environment to provide an adsorbed molecular contaminant layer upon each of the plurality of separated test sites;

means for measuring heights of the plurality of separated test sites with the adsorbed molecular contaminant layer thereon; and means for determining at least one of:

a thickness of the adsorbed molecular contaminant layer; and the base design thickness within the designed thickness interrelationship, while using an algorithm that considers the designed thickness interrelationship.

2. The test system of claim 1 wherein the algorithm includes:

$$V=(Tm-Tn)/(Km-Kn)$$

$$S=-(KnTm-KmTn)/(Km-Kn),$$

where:

V equals actual base design thickness;

S equals actual adsorbed molecular contaminant layer thickness;

Km and Kn (m, n=1, 2, 3, . . . ) are a pair of base design thickness multipliers for a pair of separated test sites; and Tm and Tn (m, n=1, 2, 3, . . . ) are measured composite thicknesses of separated test sites and adsorbed molecular contaminant layers.

3. The test system of claim 1 wherein the algorithm is a linear regression algorithm:

$$Tn=VKn+S$$

where:

V equals actual base design thickness;

S equals actual adsorbed molecular contaminant layer thickness;

Kn (n=1, 2, 3, . . . ) are base design thickness multipliers for separated test sites; and Tn (n=1, 2, 3 . . . ) are measured composite thicknesses of separated test sites and adsorbed molecular contaminant layers.

4. The test system of claim 1 wherein the base design thickness is from about 10 to about 50 angstroms and the designed thickness interrelationship provides the separated test sites with multiples of the base design thickness.

5. The test system of claim 1 wherein the means for measuring uses an ellipsometry method.

6. The test system of claim 1 wherein the means for measuring uses an optical scattering method.

7. The test system of claim 1 wherein the means for measuring uses an ion beam method.

* * * * *